US011786152B2

(12) United States Patent
Bechtel et al.

(10) Patent No.: US 11,786,152 B2
(45) Date of Patent: *Oct. 17, 2023

(54) TISSUE OXIMETRY PROBE WITH TISSUE MARKING FEATURE

(71) Applicant: ViOptix, Inc., Newark, CA (US)

(72) Inventors: Kate LeeAnn Bechtel, Pleasant Hill, CA (US); Joseph Anthony Heanue, Oakland, CA (US); Lester John Lloyd, Orinda, CA (US)

(73) Assignee: ViOptix, Inc., Newark, CA (US)

( * ) Notice: Subject to any disclaimer, the term of this patent is extended or adjusted under 35 U.S.C. 154(b) by 539 days.

This patent is subject to a terminal disclaimer.

(21) Appl. No.: 16/736,724

(22) Filed: Jan. 7, 2020

(65) Prior Publication Data

US 2020/0138348 A1 May 7, 2020

Related U.S. Application Data

(60) Division of application No. 15/214,355, filed on Jul. 19, 2016, now Pat. No. 10,524,705, which is a
(Continued)

(51) Int. Cl.
*A61B 5/1455* (2006.01)
*A61B 90/00* (2016.01)
(Continued)

(52) U.S. Cl.
CPC ........ *A61B 5/14551* (2013.01); *A61B 5/0059* (2013.01); *A61B 5/0075* (2013.01); *A61B 5/1455* (2013.01); *A61B 5/1459* (2013.01); *A61B 5/1495* (2013.01); *A61B 5/14546* (2013.01); *A61B 5/14552* (2013.01); *A61B 5/72* (2013.01); *A61B 5/7246* (2013.01);
(Continued)

(58) Field of Classification Search
CPC .............. A61B 5/1455; A61B 5/14552; A61B 5/14551; A61B 5/14546
USPC .................................................. 600/310–344
See application file for complete search history.

(56) References Cited

U.S. PATENT DOCUMENTS 4,223,680 A 9/1980 Jobsis
4,286,599 A 9/1981 Hahn et al.
(Continued)

FOREIGN PATENT DOCUMENTS

JP 5261088 10/1993
JP 10216115 A 8/1998
(Continued)

OTHER PUBLICATIONS

Alexandrakis, et al., "Accuracy of the Diffusion Approximation in Determining the Optical Properties of a Two-Layer Turbid Medium," Applied Optics, vol. 37, No. 31, Nov. 1, 1998, pp. 7403-7409.
(Continued)

*Primary Examiner* — Marjan Fardanesh
(74) *Attorney, Agent, or Firm* — Aka Chan LLP

(57) ABSTRACT

An intraoperative tissue oximetry device includes a tissue marker that includes one or more pens or one or more similar ink sources, such that the tissue marker can mark tissue according to oxygen saturation measurements made by the tissue oximetry device, thereby visually delineating regions of potentially viable tissue from regions of potentially nonviable tissue.

20 Claims, 11 Drawing Sheets

Related U.S. Application Data continuation of application No. 13/887,213, filed on May 3, 2013, now Pat. No. 9,392,978.

(60) Provisional application No. 61/682,146, filed on Aug. 10, 2012, provisional application No. 61/642,395, filed on May 3, 2012, provisional application No. 61/642,399, filed on May 3, 2012, provisional application No. 61/642,389, filed on May 3, 2012, provisional application No. 61/642,393, filed on May 3, 2012.

(51) Int. Cl.
*A61B 5/00* (2006.01)
*A61B 5/1495* (2006.01)
*A61M 35/00* (2006.01)
*A61B 5/145* (2006.01)
*A61B 90/11* (2016.01)
*A61B 5/1459* (2006.01)
*A61B 90/30* (2016.01)

(52) U.S. Cl.
CPC .............. *A61B 5/7282* (2013.01); *A61B 5/74* (2013.01); *A61B 5/742* (2013.01); *A61B 5/7405* (2013.01); *A61B 5/7475* (2013.01); *A61B 90/11* (2016.02); *A61B 90/39* (2016.02); *A61M 35/003* (2013.01); *A61B 2090/065* (2016.02); *A61B 2090/306* (2016.02); *A61B 2090/395* (2016.02); *A61B 2560/0431* (2013.01); *A61B 2560/0475* (2013.01); *A61B 2562/0271* (2013.01); *A61B 2562/166* (2013.01)

(56) References Cited

U.S. PATENT DOCUMENTS

| | | |
|---|---|---|
| 5,088,493 A | 2/1992 | Giannini et al. |
| 5,218,962 A | 6/1993 | Mannheimer et al. |
| 5,517,301 A | 5/1996 | Dave |
| 5,517,987 A | 5/1996 | Tsuchiya |
| 5,690,113 A | 11/1997 | Sliwa et al. |
| 6,056,692 A | 5/2000 | Schwartz |
| 6,070,093 A | 5/2000 | Oosta et al. |
| 6,078,833 A | 6/2000 | Hueber |
| 6,197,034 B1 | 3/2001 | Gvozdic et al. |
| 6,285,904 B1 | 9/2001 | Weber et al. |
| 6,453,183 B1 | 9/2002 | Walker |
| 6,516,209 B2 | 2/2003 | Cheng et al. |
| 6,549,284 B1 | 4/2003 | Boas et al. |
| 6,587,701 B1 | 7/2003 | Stranc et al. |
| 6,587,703 B2 | 7/2003 | Cheng et al. |
| 6,597,931 B1 | 7/2003 | Cheng et al. |
| 6,708,048 B1 | 3/2004 | Chance |
| 6,735,458 B2 | 5/2004 | Cheng et al. |
| 6,766,188 B2 | 7/2004 | Soller |
| 6,839,580 B2 | 1/2005 | Zonios et al. |
| 7,247,142 B1 | 7/2007 | Elmandjra et al. |
| 7,254,427 B2 | 8/2007 | Cho et al. |
| 7,344,587 B2 | 3/2008 | Kahn et al. |
| D567,949 S | 4/2008 | Lash et al. |
| 7,355,688 B2 | 4/2008 | Lash et al. |
| D568,479 S | 5/2008 | Mao et al. |
| 7,657,293 B2 | 2/2010 | Lash et al. |
| 8,798,700 B1 | 8/2014 | Heaton et al. |
| 2002/0019587 A1 | 2/2002 | Cheng et al. |
| 2002/0179094 A1 | 12/2002 | Perlow |
| 2004/0111016 A1 | 6/2004 | Casscells et al. |
| 2004/0260161 A1 | 12/2004 | Melker |
| 2005/0177069 A1 | 8/2005 | Takizawa et al. |
| 2005/0250998 A1 | 11/2005 | Huiku |
| 2005/0277818 A1 | 12/2005 | Myers |
| 2006/0129037 A1 | 6/2006 | Kaufman et al. |
| 2007/0149886 A1 | 6/2007 | Kohls |
| 2007/0225605 A1 | 9/2007 | Swanbom |
| 2008/0015422 A1 | 1/2008 | Wessel |
| 2008/0015424 A1 | 1/2008 | Bernreuter |
| 2008/0139908 A1 | 6/2008 | Kurth |
| 2008/0181715 A1 | 7/2008 | Cohen |
| 2008/0319290 A1 | 12/2008 | Mao et al. |
| 2009/0234209 A1 | 9/2009 | Lash et al. |
| 2009/0275805 A1 | 11/2009 | Lane et al. |
| 2010/0010486 A1 | 1/2010 | Mehta et al. |
| 2011/0028814 A1 | 2/2011 | Petersen et al. |
| 2011/0046458 A1 | 2/2011 | Pinedo et al. |
| 2011/0205535 A1 | 8/2011 | Soller et al. |
| 2011/0224518 A1 | 9/2011 | Tindi et al. |
| 2011/0237911 A1 | 9/2011 | Lamego et al. |

FOREIGN PATENT DOCUMENTS

| | | |
|---|---|---|
| JP | 11244268 A | 12/1999 |
| JP | 2006109964 | 4/2006 |
| KR | 1020000075056 | 12/2000 |
| KR | 1020090016744 | 2/2009 |
| WO | 2011008382 | 1/2011 |

OTHER PUBLICATIONS

Cen, et al., "Optimization of Inverse Algorithm for Estimating the Optical Properties of Biological Materials Using Spatially-Resolved Diffuse Reflectance," Inverse Problems in Science and Engineering, vol. 18, No. 6, Sep. 2010, pp. 853-872.

Dam, et al., "Determination of Tissue Optical Properties from Diffuse Reflectance Profiles by Multivariate Calibration," Applied Optics, vol. 37, No. 4, Feb. 1, 1998, pp. 772-778.

Farrell, et al., "Influence of Layered Tissue Architecture on Estimates of Tissue Optical Properties Obtained from Spatially Resolved Diffuse Reflectometry," Applied Optics, vol. 37, No. 10, Apr. 1, 1998, pp. 1958-1972.

Fawzi, et al., "Determination of the Optical Properties of a Two-Layer Tissue Model by Detecting Photons Migrating at Progressively Increasing Depths," Applied Optics, vol. 42, No. 31, Nov. 1, 2003, pp. 6398-6411.

Kienle, et al., "Spatially Resolved Absolute Diffuse Reflectance Measurements for Noninvasive Determination of the Optical Scattering and Absorption Coefficients of Biological Tissue," Applied Optics, vol. 35, No. 13, May 1, 1996, pp. 2304-2314.

Nichols, et al., "Design and Testing of a White-Light, Steady-State Diffuse Reflectance Spectrometer for Determination of Optical Properties of Highly Scattering Systems," Applied Optics, vol. 36, No. 1, Jan. 1, 1997, pp. 93-104.

Seo, et al., "Perturbation and Differential Monte Carlo Methods for Measurement of Optical Properties in a Layered Epithelial Tissue Model," Journal of Biomedical Optics, vol. 12(1), 014030, Jan./Feb. 2007, pp. 1-15.

Tseng, et al., "In Vivo Determination of Skin Near-Infrared Optical Properties Using Diffuse Optical Spectroscopy," Journal of Biomedical Optics, vol. 13(1), 014016, Jan./Feb. 2008, pp. 1-7.

Tseng, et al., "Analysis of a Diffusion-Model-Based Approach for Efficient Quantification of Superficial Tissue Properties," Optics Letters, vol. 35, No. 22, Nov. 15, 2010, pp. 3739-3741.

Mittnacht, et al., "Methylene Blue Administration is Associated with Decreased Cerebral Oximetry Values," Anesthesia & Analgesia, Aug. 2008, vol. 105, No. 2, pp. 549-550.

Hueber, Dennis et al., "New Optical Probe Designs for Absolute (Self-Calibrating) NIR Tissue Hemoglobin Measurements," in Proceedings of Optical Tomography and Spectroscopy of Tissue III, vol. 3597, 618-631(Jan. 1999).

WINDOW LOCATION

TISSUE OXIMETRY PROBE WITH TISSUE MARKING FEATURE

BACKGROUND OF THE INVENTION

This patent application is a divisional of U.S. patent application Ser. No. 15/214,355, filed Jul. 19, 2016, issued as U.S. Pat. No. 10,524,705 on Jan. 7, 2020, which is a continuation of U.S. patent application Ser. No. 13/887,213, filed May 3, 2013, issued as U.S. Pat. No. 9,392,978 on Jul. 19, 2016, which claims the benefit of U.S. patent applications 61/642,389, 61/642,393, 61/642,395, and 61/642,399, filed May 3, 2012, and 61/682,146, filed Aug. 10, 2012. These applications are incorporated by reference along with all other references cited in this application.

BACKGROUND OF THE INVENTION

The present invention relates generally to optical systems that monitor oxygen levels in tissue. More specifically, the present invention relates to an optical probe that includes light sources, detectors, and a marking apparatus for marking local tissue regions that are probed by the optical probe.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring, such as for hypoxia); sports and athletics purposes at a sports arena (e.g., professional athlete monitoring); personal or at-home monitoring of individuals (e.g., general health monitoring, or personal training, such as for a marathon); and veterinary purposes (e.g., animal monitoring).

In particular, assessing a patient's oxygenation state is important as it is an indicator of the state of the patient's health. Thus, oximeters are often used in clinical settings, such as during surgery and recovery, where it may be suspected that the patient's tissue oxygenation state is unstable. For example, in reconstruction surgeries, it is desirable to distinguish between tissue that is viable and non-viable to save as much viable tissue as possible. Via the use of oximeters, physicians can attempt to distinguish between viable and non-viable tissue. However, physicians typically have to remember a map of viable tissue and non-viable tissue, which may slow down medical procedures.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of molecules that can interact with light via scattering or absorption (e.g., via light-absorbing chromophores). Such chromophores include oxygenated and deoxygenated hemoglobins, melanin, water, lipid, and cytochrome. Oxygenated and deoxygenated hemoglobins are the most dominant chromophores in the spectrum range of 600 nanometers to 900 nanometers. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving measurement accuracy; reducing measurement time; lowering cost; reducing size, weight, or form factor; reducing power consumption; and for other reasons, and any combination of these.

Therefore, there is a need for oximeters that have improved form factors and that relieve physicians and medical personal of having to remember of map of tissue scanned by an oximeter.

BRIEF SUMMARY OF THE INVENTION

An intraoperative tissue oximetry device includes a pen or pens or similar ink source (or sources) such that tissue can be marked according to oxygenation measurements made by the tissue oximetry device, thereby visually delineating regions of potentially viable tissue from regions of potentially nonviable tissue.

According to an embodiment, the device is a handheld, self-contained, oximeter device. The oximeter probe is contained within a single housing including all the components, so that it is self-contained. No external connections via wires or wireless connectivity are needed. The probe has a compact size and is relatively light weight so that it can be held easily by a person's hand. The probe can include a handle for a person's hand to grip, or fingers to grip.

The probe includes a plurality of light sources configured to generate and emit light into a portion of an extended tissue region, and a plurality of detectors having a circular arrangement and configured to detect the light subsequent to reflection from the portion and generate reflectance data based on detection of the light. The handheld, self-contained, oximeter further includes a processor configured to determine the oxygen saturation of the portion based on the reflectance data, and includes a tissue marker. The tissue marker includes a dispenser that is located at substantially a center of a circle of the circular arrangement where the dispenser is configured to deposit ink onto the portion to indicate that the probe has probed the portion.

According to a specific embodiment, the dispenser is configured to deposit ink based on one or more ranges of the oxygen saturation. The processor may be configured to determine whether the oxygen saturation is in the one or more ranges and control the dispenser to deposit the ink based on the one or more ranges that the oxygen saturation is in.

According to a specific embodiment, the dispenser is configured to deposit a plurality of colors of ink; the processor is configured to control the tissue marker to deposit the colors of ink based on ranges of the oxygen saturation; and the ranges of the oxygen saturation are respectively associated with the colors of the ink. The processor may be configured to control the tissue marker to deposit the ink onto the portion, or alternatively, a user selection device, such as a switch, is configured to be activated by a user to control the tissue marker to deposit the ink.

According to another embodiment, a handheld, self-contained, oximeter includes a probe that in-turn includes: (i) a plurality of light sources configured to generate and emit light into a portion of an extended tissue region, and (ii) a plurality of detectors that has a circular arrangement and is configured to detect the light subsequent to reflection from the portion and generate reflectance data based on detection of the light. The handheld, self-contained, oximeter further includes a processor configured to determine oxygen saturation of the portion based on the reflectance data. The handheld, self-contained, oximeter further includes a tissue marker having a plurality of dispensers. The dispensers are located outside of a circle of the circular arrangement and are configured to deposit ink onto the portion to indicate that the portion has been probed by the probe.

According to one embodiment, a method of operation of a handheld, self-contained oximeter includes emitting light into tissue, detecting the light subsequent to reflection of the light from the tissue, and generating reflectance data based on detecting the light. The method further includes determining an oxygen saturation of the tissue based on the reflectance data, and determining a range of oxygen saturation from a plurality of ranges of oxygen saturation in which the oxygen saturation lies. The method includes marking the tissue with ink based on the range that the oxygen saturation is in.

Oximeter embodiments of the present invention are capable of accurately measuring oxygenation saturation of tissue and marking regions of the tissue to indicate their viability or nonviability. Relatively quickly and easily determining viability from the markings is useful for a plastic surgeon, for example, where in intraoperative situations the plastic surgeon must quickly make determinations to distinguish between tissue that can be used for reconstruction and tissue that should be removed.

With the incorporation of the tissue marker, the tissue oximetry device may be used to fully examine multiple regions of tissue for viability prior to the creation of further surgical incisions or the removal or reconstruction of tissue. The tissue marker of the present invention allows for relatively precisely marking regions of tissue based on their oxygen saturation readings thus alleviating physicians from having to recall exactly which tissue may be considered viable based on oxygenation measurements once the physician has set aside the tissue oximetry device or has moved the tissue oximetry device to other tissue regions.

In an implementation, an oximeter probe is contained within a single housing. The oximeter proble includes: a number of light or radiation sources, positioned on a probe face of the housing, configured to generate and emit light or radiation into a portion of an extended tissue region; a number of detectors, positioned on the probe face, wherein the detectors are positioned in a circular arrangement and configured to detect the light subsequent to reflection from the portion; a processor, connected to the light sources and detectors, configured to process reflectance data received from the detectors and determine oxygen saturation of the portion based on the reflectance data; a battery power source, contained within the housing and connected to the light sources, detectors, and processor; and a tissue marking component having a dispenser or inking tip or head, connected to the probe face, where the dispenser is located within the circular arrangement (e.g., inside the circle) and is configured to deposit ink onto the portion, thereby indicating that the portion has been evaluated by the probe.

In another implementation, a method of operating an oximeter probe includes: emitting light into tissue from radiation sources positioned on a probe face of the oximeter probe housing; detecting the light subsequent to reflection of the light from the tissue using from detectors sources positioned on a probe face of an oximeter probe housing; generating reflectance data based on detecting the light by way of a processor contained with the oximeter probe housing; using the processor (e.g., without needing to use an external processor), determining an oxygen saturation of the tissue based on the reflectance data; using the processor, determining a range of oxygen saturation from a plurality of ranges of oxygen saturation in which the oxygen saturation lies; and marking the tissue with ink (or other fluid) based on the range in which the oxygen saturation is in using ink (or other fluid) stored in a reservoir contained within the oximeter probe housing and a inking tip positioned on the probe face.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 8 shows the interface block of the LED PCB.

FIG. 9 shows the window location in the detector PCB for the sources S1, S2, and S3, as viewed from the component side of the detector PCB.

FIG. 10 shows a first cross-sectional view of the probe sensor assembly of FIG. 7.

FIG. 11 shows a second cross-sectional view of the probe sensor assembly of FIG. 7.

FIG. 12 shows a third cross-sectional view of view of the probe sensor assembly FIG. 7 where the optical fibers connect to the LED PCB.

DETAILED DESCRIPTION OF THE INVENTION

The present invention relates generally to a tissue oximetry device for measuring oxygen saturation in a local tissue volume. More specifically, the present invention relates to a wireless, handheld, tissue oximetry device that has self-contained optics (lights sources and detectors), computer processing, a display, a power-supply, and a tissue marker for marking tissue as the tissue is probed by the self-contained optics.

Figure 1A:
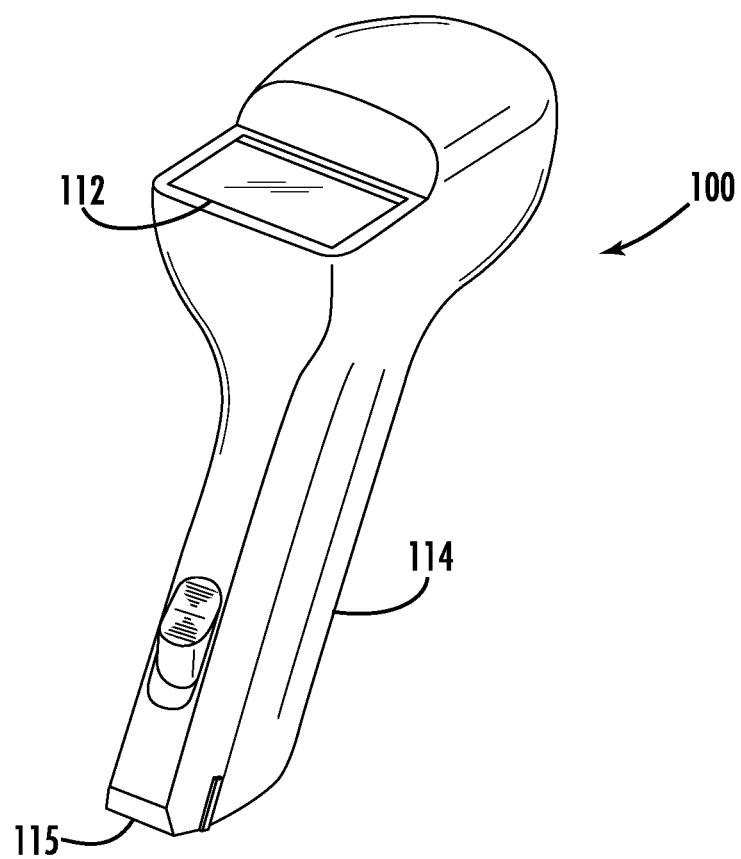
FIGS. 1A and 1B show a simplified perspective view and a top view, respectively, of a tissue oximetry device according to one embodiment.
Figure 1B:
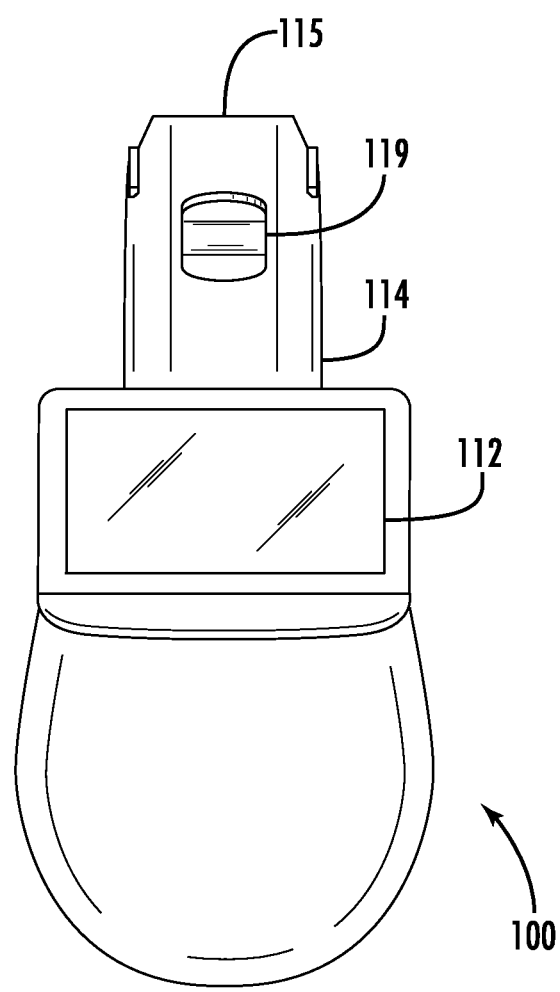

FIGS. 1A and 1B are a simplified perspective view and a top view, respectively, of a tissue oximetry device 100 according to one embodiment. The figures show an enclosure or housing of an oximeter probe device. Tissue oximetry device 100 is configured to make tissue oximetry measurements, such as intraoperatively and postoperatively.

In an implementation, the tissue oximetry device is handheld device and can make tissue oximetry measurements and display these measurements, without needing to connect to another external component either via a cable or wirelessly. The electronics to make measurements and calculations is contained entirely within the housing of the tissue oximetry device. The device may be a standalone handheld tissue oximetry device, without a cable or wireless connection.

Tissue oximetry device 100 may be a handheld device that includes a tissue oximetry probe 115 (also referred to as a sensor head), which may be positioned at an end of a sensing arm 114. Tissue oximetry device 100 is configured to measure the oxygen saturation of tissue by emitting light, such as red and near-infrared light, from tissue oximetry probe 115 into tissue, and collecting light reflected from the tissue at the tissue oximetry probe.

Tissue oximetry device 100 may include a display 112 or other notification device (e.g., a speaker for audible notification) that notifies a user of oxygen saturation values measured by the tissue oximetry device. While tissue oximetry probe 115 is described as being configured for use with tissue oximetry device 100, which is a handheld device, tissue oximetry probe 115 may be used with other tissue oximetry devices, such as a modular tissue oximetry device where the tissue oximetry probe is at the end of a cable device that couples to a base unit. The cable device might be a disposable device that is configured for use with a single patient and the base unit might be a device that is configured for repeated use. Such modular tissue oximetry devices are well understood by those of skill in the art and are not described further.

Tissue oximetry device 100 does not require a pulsing blood flow to make an oxygen saturation measurement as compared with pulse oximeters that require a pulsing blood flow to make such measurements. While the description of the example embodiments is directed toward tissue oximetry probes that do not require a pulsing blood flow for oxygen saturation measurements, embodiments of the present invention are not so limited and may be utilized with pulse oximeters.

Figure 1C:
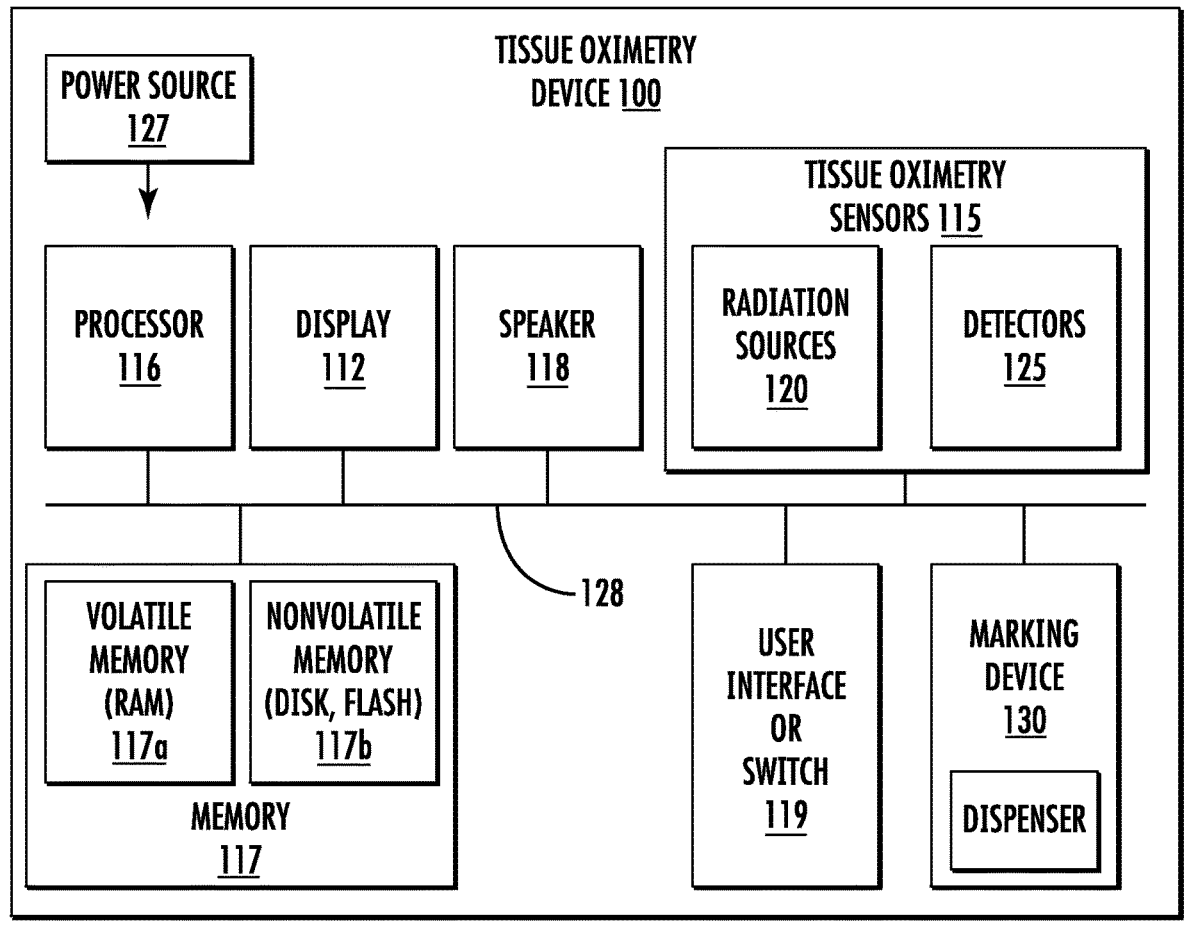
FIG. 1C shows a block diagram of the tissue oximetry device.

FIG. 1C is a block diagram that shows tissue oximetry device 100 in further detail according to one embodiment. The components of device 100 are contained in a single enclosure or housing. Tissue oximetry device 100 may include display 112, a processor 116, a memory 117, a speaker 118 (described briefly above), one or more input devices 119 (e.g., one or more switches, input buttons, keypad, display 112, if for example, the display is a touch screen, or the like), a set of light sources 120, a set of detectors 125, a power source 127, and a tissue marker 130. Processor 116 may be a microcontroller, a microprocessor, control logic, a multicore processor, or the like, and may control the operation of light sources 120 and detectors 125. Processor 116 may also control the operation of tissue marker 130. Memory 117 may include a variety of memories, such as a volatile memory 117a (e.g., a RAM), a nonvolatile memory 117 (e.g., a disk, Flash, PROM, or others), or both. User input may be by way of the input devices 119 (e.g., switches, touchpad, or the like).

Power source 127 can be a battery, such as a disposable battery. Disposable batteries are discarded after their stored charge is expended. Some disposable battery chemistry technologies include alkaline, zinc carbon, or silver oxide. The battery has sufficient stored charged to allow use of the tissue oximetry device for several hours. After use, the tissue oximetry device is discarded.

In other implementations, the battery can also be rechargeable where the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the tissue oximetry device can include a recharger circuit (not shown). Batteries with rechargeable battery chemistry may be sometimes used as disposable batteries, where the batteries are not recharged but disposed of after use.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

The components may be linked together via a bus 128, which may be the system bus architecture of tissue oximetry device 100. Although this figure shows one bus that connects to each component, the busing is illustrative of any interconnection scheme serving to link these components or other components included in tissue oximetry device 100. For example, speaker 118, according to one specific implementation, could be connected to a subsystem through a port or have an internal direct connection to processor 116.

The foregoing listed components may be housed in a mobile housing (see FIG. 1A) of tissue oximetry device 100. However, different implementations of tissue oximetry device 100 may include alternative housing (such as the cables and the base units of modular oximeters described briefly above) and may include any number of the listed components, in any combination or configuration, and may also include other components not shown.

Tissue Oximetry Probe

Figure 2A:
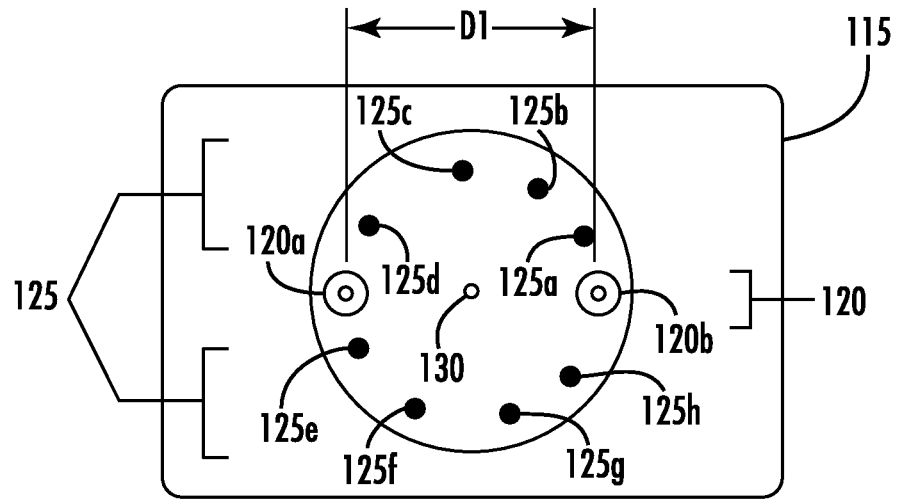
FIG. 2A shows a simplified end view of a tissue oximetry probe of the tissue oximetry device according to one embodiment where the ink dispenser is centered on the tissue oximetry probe.

FIG. 2A is a simplified end view of tissue oximetry probe 115 according to one embodiment. Tissue oximetry probe 115 is configured to contact tissue (e.g., a patient's skin) for which a tissue oximetry measurement is to be made. Tissue oximetry probe 115 includes the set of light sources 120 and the set of detectors 125. The set of light sources 120 may include two or more light sources, such as light sources 120a and 120b.

Light sources 120 may be linearly positioned across tissue oximetry probe 115 and detectors 125 may be arranged in an arc or a circle (i.e., circular arrangement) on the tissue oximetry probe. More specifically, light sources 120 may be arranged linearly, such as on a line (e.g., a diameter) that bisects a circle on which detectors 125 may be arranged. The light sources 120a and 120b are spaced a distance D1 apart where D1 may range from about 3 millimeters to about 10 millimeters. That is, the circle on which detectors 125 are arranged may have a diameter of about 3 millimeters to about 10 millimeters (e.g., 4 millimeters according to one specific embodiment). While detectors 125 are described as being arranged in an arc or circle, tissue oximetry device 100 may have other configurations of detectors, such as linear, square, rectangular, ovoid, pseudo-random, or others.

Propagation depth increases with increasing source-to-detector distance, with 4-5 millimeters generally being a sufficient upper limit between light sources 120a and detectors 125 to ensure few detected photons propagated in lower tissue layers. For example, these distances between light sources 120 and detectors 125 limits reflectance data to light that propagated within the top layer of tissue where little or no underlying subcutaneous fat or muscular layers contributes to the reflectance data.

The set of detectors 125 may include four or more detectors. According to a specific embodiment, the set of detectors 125 includes eight detectors 125a, 125b, 125c, 125d, 125e, 125f, 125g, and 125h as shown. Detectors 125 are solid-state detectors and may be mounted to a PCB (not shown). Further, detectors 125 may be combined devices or discrete devices.

In a specific implementation, detectors 125 are positioned with respect to outer light sources 120a and 120c such that four or more (e.g., fourteen) unique source-to-detector distances are created. With greater numbers of source-to-detector distances, this can be used to obtain greater accuracy, faster calibration, and redundancy (when duplicate source-to-detector distances are provided). At least two source-to-detectors distances are 1.5 millimeters or closer, and at least two more two source-to-detectors distances are 2.5 millimeters or farther.

In other words, a first source-to-detector distance is about 1.5 millimeters or less. A second source-to-detector distance is about 1.5 millimeters or less. A third source-to-detector distance is about 2.5 millimeters or greater. A fourth source-to-detector distance is about 2.5 millimeters or greater. There can be various numbers of sources and detector arrangements to obtain these four source-to-detector distances, such as one source and four detectors, two sources and two detectors, one detector and four sources, or other arrangements and combinations.

For example, an implementation includes at least two sources and at least two detectors, where a maximum distance between a source and a detector is about 4 millimeters (or about 5 millimeters). At least two source-to-detector are about 2.5 millimeters or greater. At least two source-to-detector distances are about 1.5 millimeters or less.

When a greater number of sources and detectors are used, greater numbers of source-to-detector distances are available. As discussed, these can be used to provide greater accuracy, faster calibration, or redundancy, or a combination. The arrangement of the sources and detectors can be in circular pattern, such as at points along the arc of a circle with radius (e.g., 4 millimeters, or 5 millimeters). In an implementation, a tolerance of the detector or source positions on the arc is within 10 microns of the arc curve. In other implementations, the tolerance is within about 0.25 millimeters.

Tissue Marking

Turning now to tissue marker 130, tissue oximetry probe 115 includes at least a dispenser portion of tissue marker 130. FIG. 2 shows an end view of the dispenser that can dispense a marking material on a local tissue region (e.g., of an extended portion of tissue) that has been probed by tissue oximetry device 100. The location of the marking material on tissue allows a user to subsequently identify the particular, local tissue region that has been probed.

The dispenser may be located at a variety positions on the face of tissue oximetry probe 115. According to one specific embodiment, the dispenser is located between light sources 120a and 120b, and may be located at the approximate center of the circular arrangement of detectors 125. With the dispenser at the approximate center of light sources 120 and detectors 125, a mark made by the dispenser will be substantially at a center of the local tissue region that has been probed by tissue oximetry device 100. With the mark at the center of the probed tissue region, the mark is not displaced from the location on the local tissue region probed.

Figure 2B:
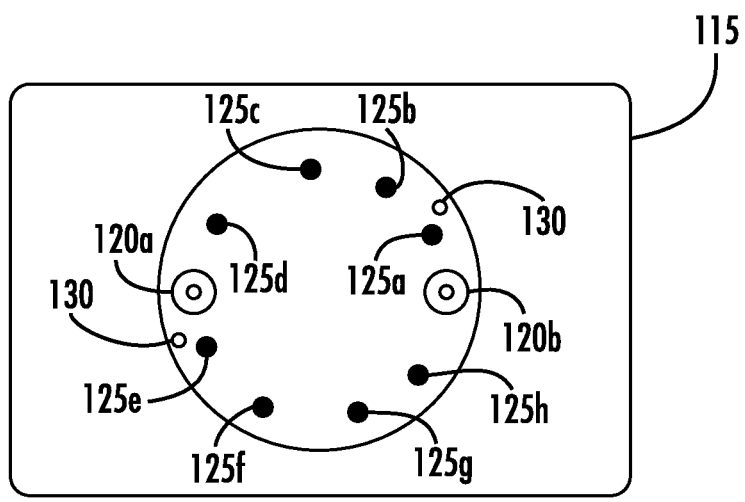
FIG. 2B shows a simplified end view of the tissue oximetry probe where first and second dispensers are located outside of a circle of detectors.

According to one implementation, tissue marker 130 includes one or more dispensers that may be located at different positions on the head of tissue oximetry probe 115. FIG. 2B shows an embodiment where two dispensers are located "outside" of light sources 120 and detectors 125. That is, the dispensers are located at the ends of radii that are longer than the radii of light sources 120 and detectors 125. Further, the dispensers may lie on a line that passes through the center of the circle of the circular arrangement of dispensers 125. With the dispensers located along such a line, marks made by these dispensers allow a user to readily identify the region between the marks as the local tissue region that has been probed by tissue oximetry device 100.

While the dispensers shown in FIGS. 2A and 2B are shown as relatively localized devices (e.g., pen, pens, inker, inkers, and the like) that may be configured to mark tissue with relatively small marks (e.g., dots), a dispenser may be an extended device configured to make an extended mark, such as a line. For example, a dispenser may be an extended device configured to mark tissue with a circle or other closed shape, or may mark tissue with an open shape, such as a u-shape, a v-shape, or others.

The dispenser may be fixed within tissue oximetry probe 115 or may be configured to be lowered when tissue is marked. Various mechanical or electromechanical devices may be utilized by tissue oximetry probe 115 for lowering the dispenser. Such mechanical and electro-mechanical devices are well understood by those of skill in the art and are not described in detail herein.

Tissue marker 130 may mark tissue with a variety inks having a variety of colors, such as gentian violet, which is the tissue marking ink approved by the FDA. Variations in the gentian violet chemistry constituents can give different characteristics to the ink and cause changes in color or shade. Any of these colors or shades of gentian violet may be utilized by tissue marker 130.

One or more of the ink colors utilized by tissue oximetry device 100 may indicate one or more oxygen saturation ranges. For example, tissue marker 130 might be configured to: (i) mark tissue with a first color of ink if the tissue's oxygen saturation is at or below a first threshold, (ii) mark the tissue with a second color of ink if the tissue's oxygen saturation is above the first threshold and at or below a second threshold, and (iii) mark the tissue with a third color of ink if the tissue's oxygen saturation is above the second threshold. The foregoing example describes the use of three colors of ink for marking tissue for visually identifying three ranges of oxygen saturation, however more or fewer colors may be utilized by tissue marker 130 for identifying more or fewer oxygen saturation ranges.

Processor 116 may determine the oxygen saturation of a local tissue region based on an analysis of the reflection data that has been generated by detectors 125, and may control tissue marker 130 to mark the local tissue region with a select color of ink that identifies the range that the oxygen saturation is within. Tissue marker 130 may include a variety of devices that provide marking material having one or more colors, such as ink reservoirs, pens, or the like. U.S. patent application Ser. No. 12/178,359, filed Jul. 23, 2008, of Heaton, titled "Oximeter with Marking Feature", which is incorporated by reference in its entirety, describes a variety of devices that are configured for marking tissue with one or more colors of marking material.

A reservoir of the marking device can be connected to the dispenser, such as through tubing or channels, and is contains ink or other fluid (e.g., ink) dispensed through the dispenser. Ink can be urged from the reservoir to and through the dispenser and deposited on skin through pressure or low-frequency sound (such using a piezoelectric transducer). The reservoir is contained within the same housing as the processor, battery, sources, detectors, and other components of the oximeter probe. For the disposable probe, the reservoir is not refillable.

According to one alternative, tissue marker 130, under control of processor 116, marks tissue for one or more oxygen saturation ranges, but does not mark the tissue for one or more other oxygen saturation regions. For example, tissue marker 130 might mark a local tissue region if the oxygen saturation of the local tissue region is at or below a threshold level, or alternatively might not mark the local tissue region if the oxygen saturation level is above the threshold level. Markings that are made on tissue according to the above method allow a user to relatively quickly identify tissue that might have a low chance of viability if the threshold level is relatively low. Alternatively, tissue marker 130 might mark a local tissue region if the oxygen saturation of the local tissue region is at or above a threshold level, and might not mark the local tissue region if the oxygen saturation level is below the threshold level. Marks made from this method allow a user to relatively quickly identify tissue that might have a relatively high chance of viability if the threshold level is relatively high.

Information for the foregoing described threshold levels (i.e., ranges) may be stored in memory 117 and accessed by processor 116 for use. The threshold levels may be stored in memory 117 during manufacture of tissue oximetry device 100, or may be stored in the memory thereafter. For example, tissue oximetry device 100 may be configured to receive a user input for one or more user defined threshold levels and store information for these threshold levels in memory 117. One or more input devices 119 (or the like) may be configured to receive a user input for a user defined threshold level and for storing the user defined threshold level in memory 117.

Figure 2C:
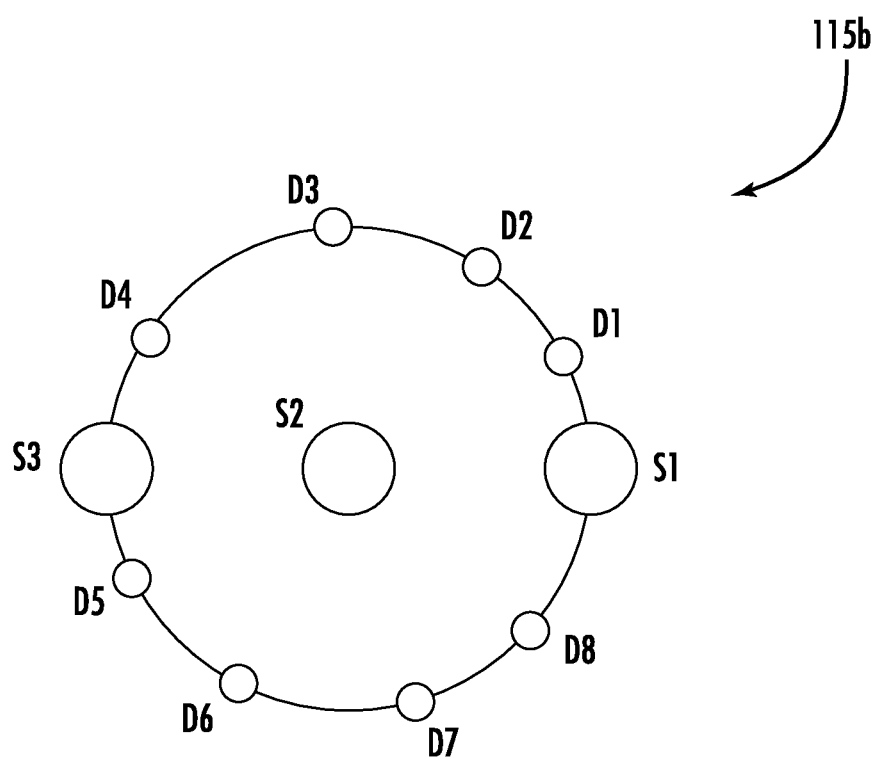
FIG. 2C shows a tissue oximetry probe geometry for robust calibration and self-correction. In this figure, S2-detector distances are all equal and there are 14 unique distances between S1-detectors and S3-detectors combined (S1D1=S3D5 and S1D5=S3D1).

FIG. 2C shows an implementation of the geometry of a tissue oximetry probe 115b for robust calibration and self-correction. The S2-detector (second source to detector) distances are all equal for tissue oximetry probe geometry 115b. There are 14 unique distances between S1-detectors (first source to detectors) and S3-detectors (third source to detectors) combined for tissue oximetry probe geometry 115b. Further, the distance between the first source and first detector is equal to the distance between the third source and the fifth detector (S1D1=S3D5), and the distance between the first source and fifth detector is equal to the distance between the third source and the first detector (S1D5=S3D1).

Figure 3:
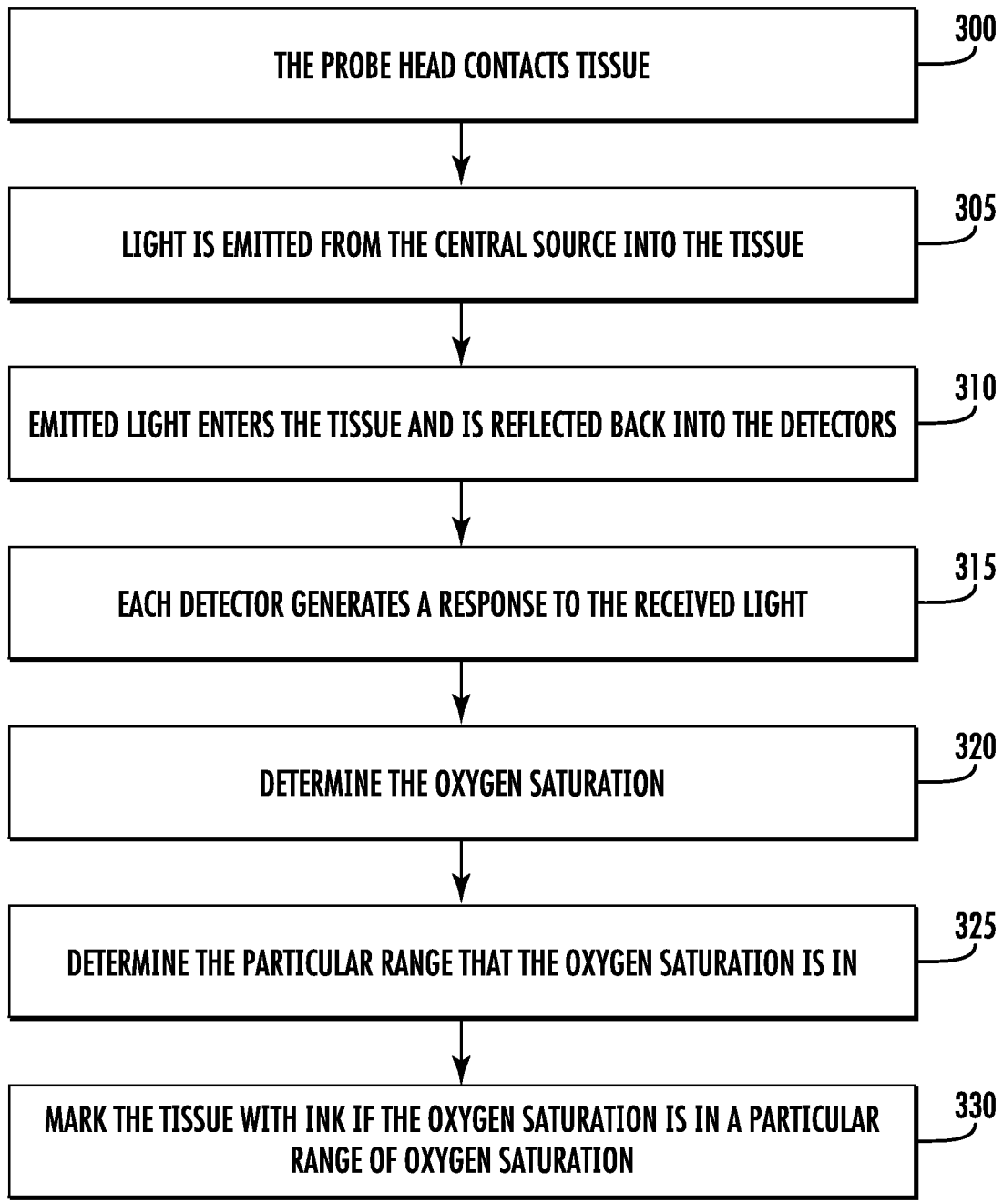
FIG. 3 shows a high-level flow diagram of a method for marking tissue to indicate ranges of oxygen saturation of the tissue.

FIG. 3 is a high-level flow diagram of a method for marking tissue to indicate ranges of oxygen saturation of the tissue. The high-level flow diagram represents one example embodiment. Steps may be added to, removed from, or combined in the high-level flow diagram without deviating from the scope of the embodiment.

At 300, tissue oximetry probe 115 contacts the tissue. Light (e.g., near-infrared light) is emitted from one or more of the light sources 120, step 305, into the tissue and at least some of the light is reflected back by the tissue. Each detector 125 receives a portion of the light reflected from the tissue, step 310, and each detector generates reflectance data (i.e., a response) for the portion of reflected light received, step 315. At 320, processor 305 determines an oxygen saturation value for the tissue based on the reflectance data. At 325, processor 116 determines a range of oxygen saturation from a plurality of ranges of oxygen saturation in which the oxygen saturation lies. At 330, processor 116 controls tissue marker 130 to mark the tissue with ink based on a range in which the oxygen saturation is in. For example, the processor may be configured to control the dispenser to mark the tissue with ink if the oxygen saturation is in a first range of oxygen saturation, but not mark the tissue if the oxygen saturation in a second range of oxygen saturation where the first range and second range are different, such as not overlapping ranges. While the foregoing example embodiment, discusses the utilization of two ranges of oxygen saturation by the tissue oximetry device, the tissue oximetry device may utilize more than two ranges of oxygen saturation for determining whether to mark the tissue with ink.

According to one embodiment, the processor may control the dispenser to mark the tissue with a specific color of ink based on the range of oxygen saturation that the oxygen saturation is in. The particular color of ink allows a user to relatively quickly determine the ranges of oxygen saturation for the tissue without the need for re-probing the tissue or looking at a chart of the tissue that includes oxygen saturation values and matching the chart to the tissue.

Figure 4:
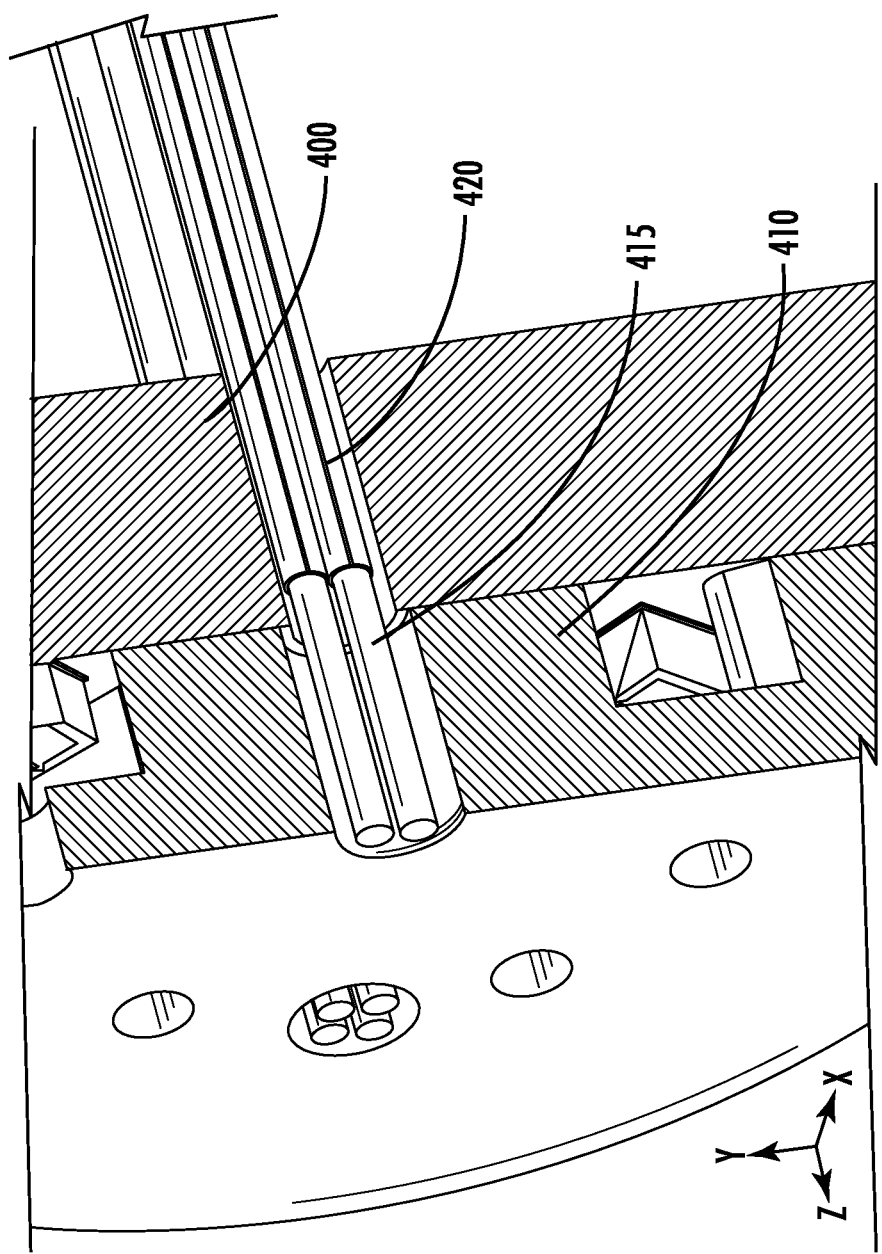
FIG. 4 shows a cross-sectional view of the probe sensor assembly of the tissue oximetry device in one implementation.

FIG. 4 shows a cross-sectional view of a probe sensor assembly 115 of the tissue oximetry device in one implementation. The probe sensor assembly includes a printed circuit board (PCB) 400 with an aperture 410. There are optic fibers having fiber cores 415 where each fiber core is positioned within a jacket. The optical fibers run through the PCB.

Figure 5:
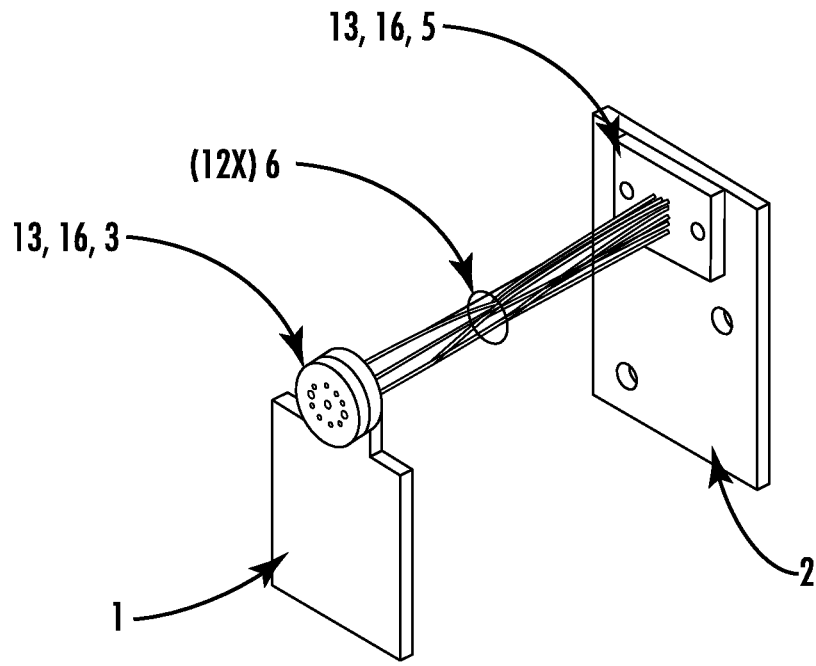
FIGS. 5-6 show views of an LED board and a detector board of the probe sensor assembly 115. There are optical fiber connections between the LED and detector boards, which connect to the sensor openings.
Figure 6:
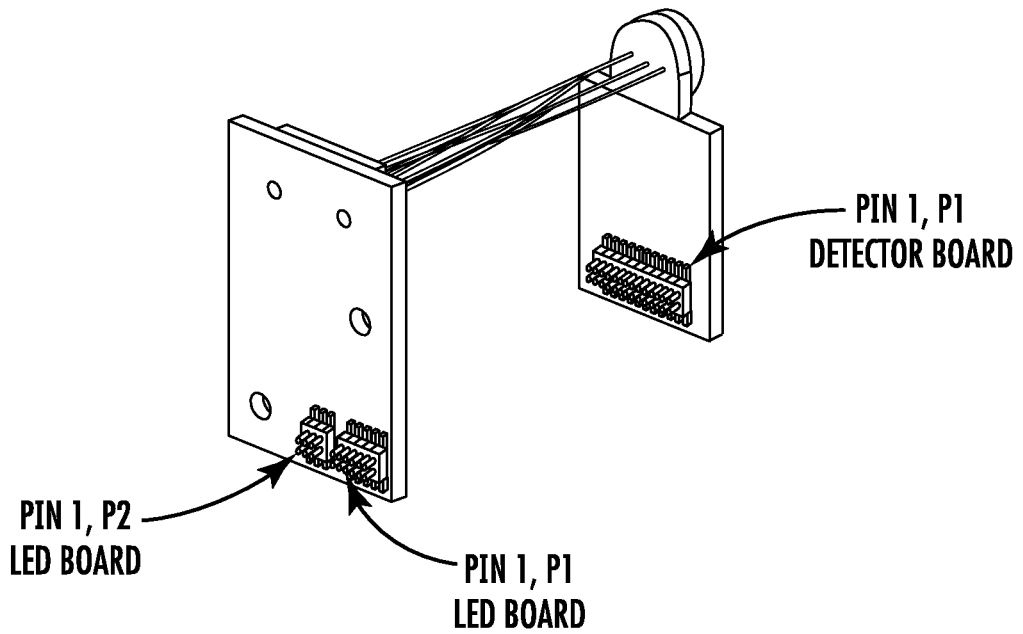
Figure 7:
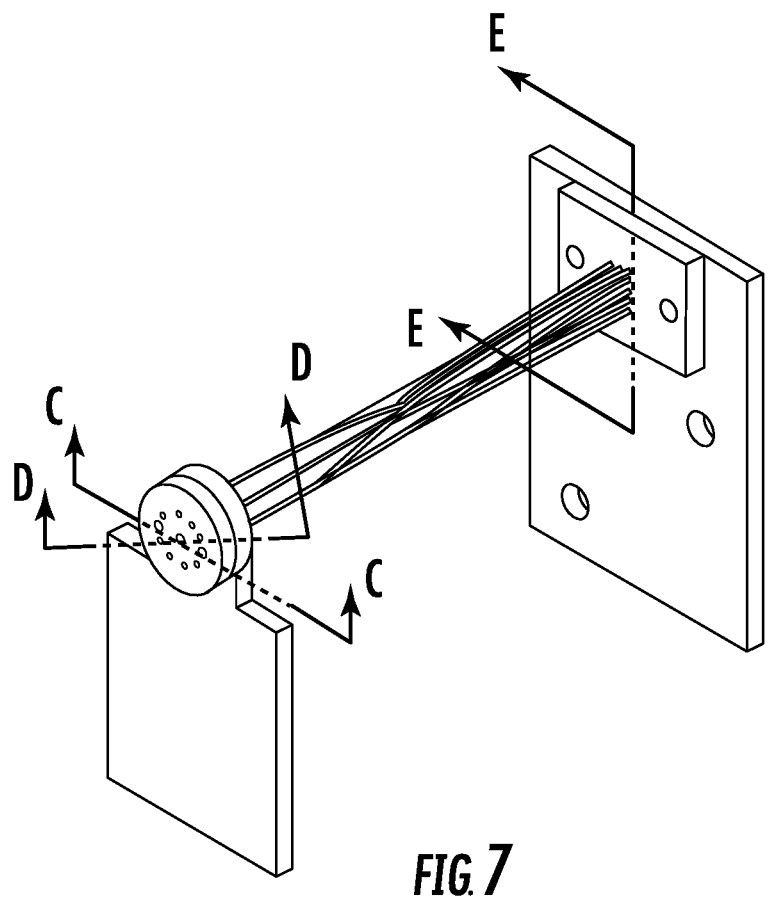
FIGS. 7-12 show fiber optic connections of the probe sensor assembly in an implementation of the tissue oximeter device.

FIGS. 5-6 show views of an LED board and a detector board of the probe sensor assembly 115. There are optical fiber connections between the LED and detector boards, which connect to the sensor openings.

Figure 8:
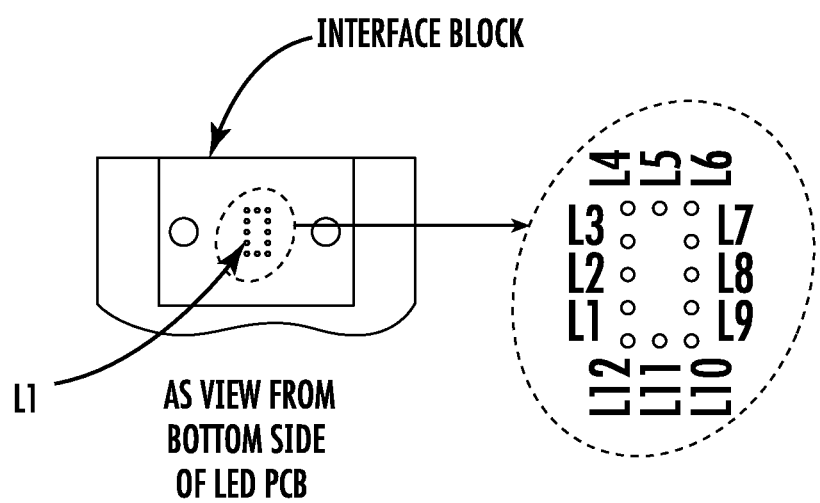

FIGS. 7-12 show the fiber optic connections of the probe sensor assembly 115 in an implementation. FIG. 8 shows the interface block of the LED PCB.

Figure 9:
Figure 10:
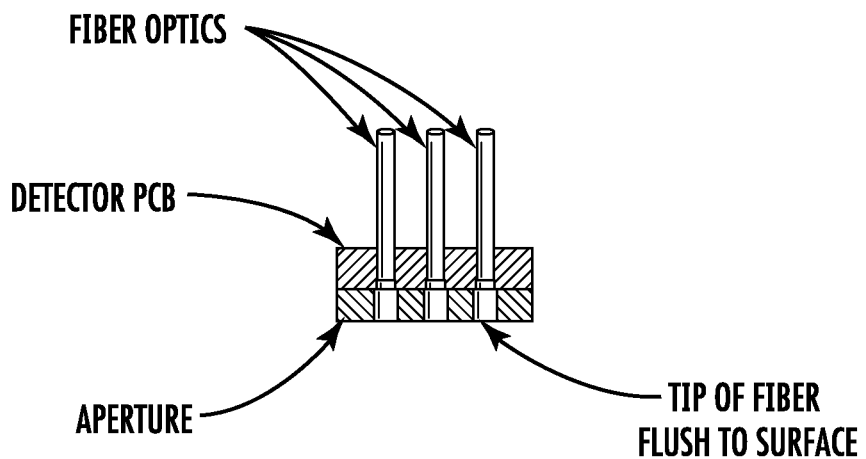
Figure 11:
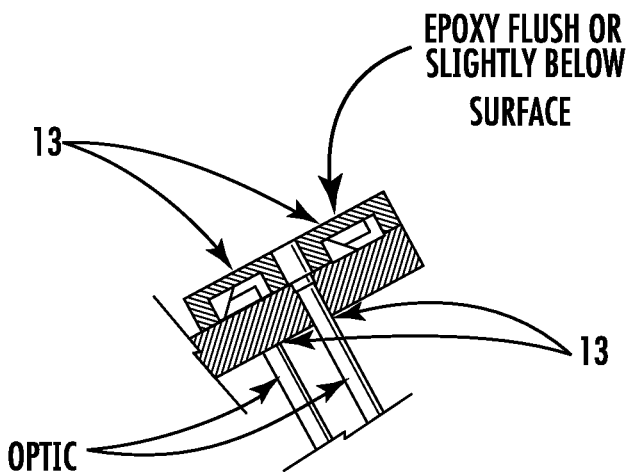
Figure 12:
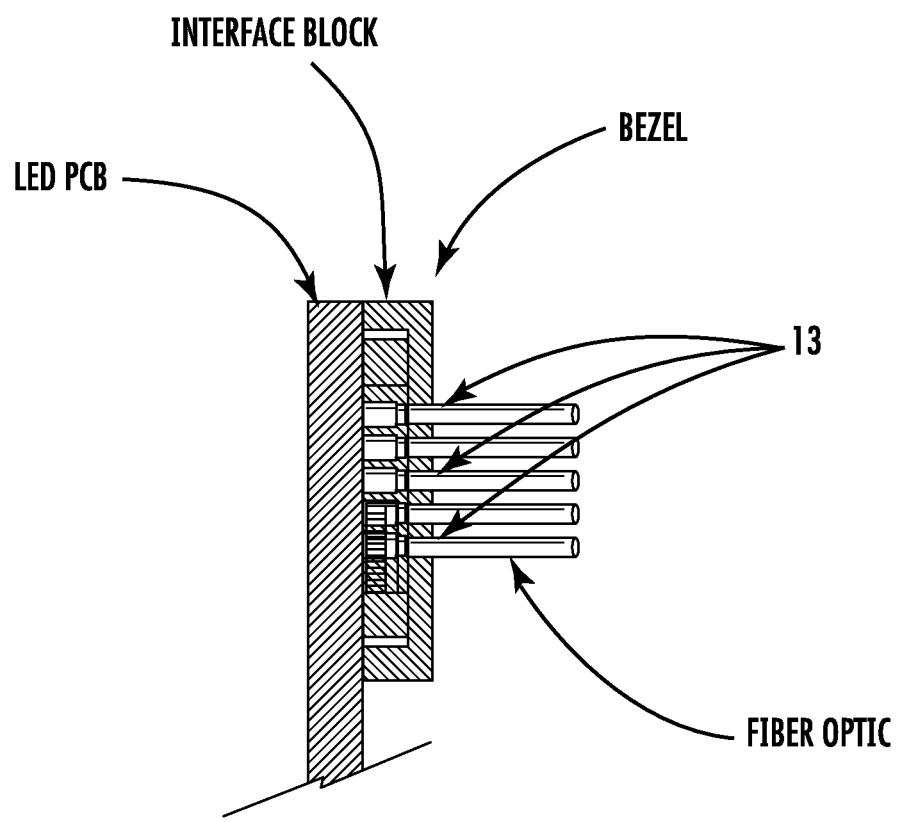

FIG. 9 shows the window location in the detector PCB for the sources S1, S2, and S3, as viewed from the component side of the detector PCB. FIG. 10 shows the cross-sectional view C-C of FIG. 7 where the optical fibers enter the detector PCB and the tips of the optical fibers are flush with the surface of the aperture plate. FIG. 11 shows the cross-sectional view D-D of FIG. 7. FIG. 12 shows the cross-sectional view E-E of FIG. 7 where the optical fibers connect to the LED PCB of the probe sensor assembly.

Tissue oximetry device 100 may be configured to allow a user to manually control the tissue oximetry device to mark tissue, allow processor 116 to control marking the tissue, or both. For example, one of input devices 119 may be configured to control tissue marker 130 to mark a local tissue region if a user activates the input device. The input device may be conveniently located for a user to operate tissue oximetry device 100 to make an oxygen saturation measurement, and operate the input device without moving tissue oximetry probe 115 from the local tissue region that was probed.

Tissue oximetry device 100 may be switched between the processor controlled method of marking tissue and the manually controlled method (e.g., activating one of the switches) of marking tissue. One or more other of input devices 119 may be configured for switching tissue oximetry device 100 between these two methods of marking tissue.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A tissue oximetry device comprising:
a housing comprising:
a processor contained within the housing;
a memory, contained within the housing, wherein the memory is coupled to the processor;
a display, coupled to the processor, wherein the display is visible from an exterior of the housing; and
a tissue marking component contained within the housing, wherein the tissue marking component is coupled to the processor; and
a tip portion of the housing;
a sensor module, coupled to the processor, wherein the sensor module comprises a probe face that is retained by the tip portion of the housing at a relatively fixed position with respect to the housing and that is placed against and faces tissue to be measured, and the sensor module comprises:
a first dispenser formed on the probe face and connected to the processor and the tissue marking component;
a first source structure and a second source structure, each formed on the probe face;
a first source diode and a second source diode, each coupled to the processor;
a first radiation directing element and a second radiation directing element, optically coupled, respectively, to the first and second source diodes;
a first optical fiber optically coupled between the first radiation directing element and the first source structure;
a second optical fiber optically coupled between the second radiation directing element and the second source structure, wherein the first optical fiber transmits radiation emitted by the first source structure and passed through the first radiation directing element to the first source structure, and the second optical fiber transmits radiation emitted by the second source structure and passed through the second radiation directing element to the second source structure;
a first detector structure, formed on the probe face, wherein a first distance is from the first detector structure to the first source structure, a second distance is from the first detector structure to the second source structure, and the first distance is greater than the second distance;
a second detector structure, formed on the probe face, wherein a third distance is from the second detector structure to the first source structure, a fourth distance is from the second detector structure to the second source structure, and the fourth distance is greater than the third distance;
a third detector structure, formed on the probe face, wherein a fifth distance is from the third detector structure to the first source structure, a sixth distance is from the third detector structure to the second source structure, the fifth distance is different from the first distance and the second distance, and the sixth distance is different from the first distance and the second distance; and
a fourth detector structure, formed on the probe face, wherein the first and second detector structures are arranged symmetrically about a point on a line on which the first and second source structures are arranged, the third and fourth detector structures are arranged symmetrically about the point on the line, a seventh distance is from the fourth detector structure to the first source structure, an eighth distance is from the fourth detector structure to the second source structure, the seventh distance is different from the first, second, and fifth distances, and the eighth distance is different from the first, second, and sixth distances,
the first distance is different from the second, third, and fourth distances,
the second distance is different from the third and fourth distances,
the third and fourth distances are different,
the first distance is greater than the second, third, fifth, sixth, seventh, and eighth distances, and the second distance is less than the fifth, sixth, seventh, and eight distances,
the first dispenser is located on the point on the line and between the first and second source structures, and
wherein the processor is adapted to process reflectance data received from the detector structures for the tissue, determine an oxygen saturation value for the tissue based on the reflectance data, control the display to display an indicator for the oxygen saturation value, and control the tissue marking component for dispensing a first marking material from the dispenser if the oxygen saturation value is within a first range of oxygen saturation values and not within a second range oxygen saturation values, and the first and second ranges of oxygen saturation values are different ranges of oxygen saturation values.

2. The device of claim 1 wherein a ninth distance is from the first source structure to the second source structure, and the ninth distance is greater than the first, second, fifth, sixth, seventh, and eighth distances.

3. The device of claim 1 wherein the processor is adapted to control the tissue marking component for not dispensing the first marking material from the dispenser if the oxygen saturation value is not within the first range of oxygen saturation values.

4. The device of claim 1 wherein the processor is adapted to control the tissue marking component for dispensing a second marking material from the dispenser onto the tissue if the oxygen saturation value is within the second range of oxygen saturation values, and the first and second marking materials have first and second colors that are different colors.

5. The device of claim 4 wherein information for the first and second ranges of the oxygen saturation values are previously stored in the memory.

6. The device of claim 4 wherein information for the first and second ranges of the oxygen saturation values are user programmable.

7. The device of claim 1 wherein the first dispenser is positioned at a center point on the line that is between the first and second source structures, the first and second detector structures are arranged symmetrically about the center point, and the third and fourth detector structures are arranged symmetrically about the center point on the line.

8. The device of claim 1 comprising a second dispenser, coupled to the tissue making component, formed on the probe face, wherein the first and second dispensers are positioned outside of a circle of a circular arrangement of the first, second, third, and fourth detector structures.

9. The device of claim 1 wherein the processor is adapted to initiate movement of the first dispenser from a first position to a second position in the sensor module, in the second position the dispenser is configured to deposit the first marking material onto the tissue, and in the first position the dispenser is not configured to deposit the first marking material onto the tissue.

10. The device of claim 1 wherein the tissue oximetry device is a standalone unit, when the tissue oximetry device is used, the housing comprising the processor, memory, display, and battery of the device is cradled on a purlicue between a thumb and forefinger of a hand of a user while the display is at a proximal end of the device and the tip portion of the housing extends in a distal direction to a distal end of the device, and
while the device is in the user's hand, the user positions the probe face that is at the distal end of the device on the tissue to be measured.

11. A device comprising:
an oximeter probe contained within a single housing comprising:
a plurality of light sources configured to generate and emit light into a portion of an extended tissue region;
a plurality of detectors having a circular arrangement, and are configured to detect the light subsequent to reflection from the portion and generate reflectance data based on detection of the light;
a processor configured to determine oxygen saturation of the portion based on the reflectance data;
a tissue marker having a plurality of dispensers, wherein the dispensers are coupled to the processor and are located outside of a circle of the circular arrangement of the detectors and are configured to deposit ink onto the portion,
the dispensers are configured to deposit ink based on one or more ranges of the oxygen saturation,
the processor is configured to determine whether the oxygen saturation is in the one or more ranges and control the dispensers to deposit the ink based on the one or more ranges that the oxygen saturation is in; and
a user selection device configured to be activated by a user, wherein activation of the user selection device controls the tissue marker to deposit the ink onto the portion.

12. The device of claim 11 wherein the dispensers are configured to deposit a plurality of colors of ink,
the processor is configured to control the tissue marker to deposit the colors of ink based on the ranges of the oxygen saturation, and
the ranges of the oxygen saturation are respectively associated with the colors of the ink.

13. A tissue oximetry device comprising:
a housing comprising:
a processor contained within the housing;
a memory, contained within the housing, wherein the memory is coupled to the processor;
a display, coupled to the processor, wherein the display is visible from an exterior of the housing; and
a tissue marking component, contained within the housing, wherein the tissue marking component is coupled to the processor; and
a tip portion of the housing;
a sensor module, coupled to the processor, wherein the sensor module comprises a probe face that is retained by the tip portion of the housing at a relatively fixed position with respect to the housing and that is placed against and faces tissue to be measured, and the sensor module comprises:
a first dispenser formed on the probe face and connected to the processor and the tissue marking component;
a first plurality of detector structures, formed on the probe face, arranged symmetrically about a point on a line;
a second plurality of detector structures, formed on the probe face, arranged symmetrically about the point on the line;
a first source structure, formed on the probe face, positioned at a first position on the line;
a second source structure, formed on the probe face, positioned at a second position on the line, wherein the first dispenser is positioned at a third position on the line and the third position is between the first and second positions;
a first source diode and a second source diode;
a first optical fiber optically coupled between the first source diode and the first source structure;
a second optical fiber optically coupled between the second source diode and the second source structure, wherein the first optical fiber transmits radiation emitted by the first source diode to the first source structure, and the second optical fiber transmits radiation emitted by the second source diode to the second source structure;
a first detector structure of the first plurality of detector structures, wherein a first distance is from the first detector structure to the first source structure, a second distance is from the first detector structure to the second source structure, and the first distance is greater than the second distance;
a second detector structure of the first plurality of detector structures, arranged symmetrically with respect to the first detector structure about the point on the line, wherein a third distance is from the second detector structure to the first source structure, a fourth distance is from the second detector structure to the second source structure, and the fourth distance is greater than the third distance;
a third detector structure of the second plurality of detector structures, arranged asymmetrically with respect to the first plurality of detectors structures about the point on the line, wherein a fifth distance is from the third detector structure to the first source structure, a sixth distance is from the third detector structure to the second source structure, the fifth distance is different from the first distance and the second distance, and the sixth distance is different from the first distance and the second distance; and
a fourth detector structure of the second plurality of detector structures, arranged asymmetrically with respect to the first plurality of detectors structures and the third detector structure about the point on the line, wherein a seventh distance is from the fourth detector structure to the first source structure, an eighth distance is from the fourth detector structure to the second source structure, the seventh distance is different from the first, second, and fifth, and the eighth distance is different from the first, second, and sixth distances, the first distance is different from the second, third, and fourth distances, the second distance is different from the third and fourth distances, the third and fourth distances are different, the first distance is greater than the second, third, fifth, sixth, seventh, and eighth distances, and the second distance is less than the fifth, sixth, seventh, and eight distances, and wherein the processor is adapted to process reflectance data received from the detector structures, determine an oxygen saturation value for the tissue based on the reflectance data, control the display to display an indicator for the oxygen saturation value, and control the tissue marking component for dispensing a first marking material from the dispenser if the oxygen saturation value is within a first range of oxygen saturation values and not within a second range of oxygen saturation values, and the first and second ranges of oxygen saturation values are different ranges.

14. The device of claim 13 wherein a ninth distance is from the first source structure to the second source structure, and the ninth distance is greater than the first, second, fifth, sixth, seventh, and eighth distances.

15. The device of claim 13 wherein information for the first and second ranges of the oxygen saturation values are previously stored in the memory.

16. The device of claim 13 wherein information for the first and second ranges of the oxygen saturation are user programmable.

17. The device of claim 13 comprising a user selection device configured to be activated by a user, wherein activation of the user selection device controls the tissue making component to allow deposit of the first marking material onto the tissue to be measured via the first dispenser.

18. The device of claim 13 comprising a user selection device configured to initiate movement of the first dispenser from a first position to a second position in the sensor module, wherein in the first position the dispenser is configured not to deposit the first marking material onto the tissue, and in the second position the dispenser is configured to deposit the first marking material onto the tissue.

19. A method of operating a tissue oximeter device comprising:

emitting light into tissue from a first source structure and a second source structure, wherein the first and second source structures are formed on a probe face of a sensor module that is retained by a tip portion of an oximeter probe housing at a relatively fixed position with respect to the oximeter probe housing, the first and second source structures are positioned on a line;

detecting the light subsequent to reflection of the light from the tissue using a first detector structure, a second detector structure, a third detector structure, and a fourth detector structure each formed on the probe face, wherein the first and second source structures are symmetrically positioned about a point on the line, and the third and fourth source structures are symmetrically positioned about the point on the line, wherein a first distance is from the first detector structure to the first source structure, a second distance is from the first detector structure to the second source structure, and the first distance is greater than the second distance, a third distance is from the second detector structure to the first source structure, a fourth distance is from the second detector structure to the second source structure, and the fourth distance is greater than the third distance, a fifth distance is from the third detector structure to the first source structure, a sixth distance is from the third detector structure to the second source structure, the fifth distance is different from the first distance and the second distance, and the sixth distance is different from the first distance and the second distance, a seventh distance is from the fourth detector structure to the first source structure, an eighth distance is from the fourth detector structure to the second source structure, the seventh distance is different from the first, second, and fifth, and the eighth distance is different from the first, second, and sixth distances, the first distance is different from the second, third, and fourth distances, the second distance is different from the third and fourth distances, the third and fourth distances are different, the first distance is greater than the second, third, fifth, sixth, seventh, and eighth distances, and the second distance is less than the fifth, sixth, seventh, and eight distances; and powering the first and second source structures with a battery housed within the oximeter probe housing to emit the light into the tissue;

powering the first, second, third, and fourth detector structures with the battery to detect the light reflected from the tissue;

generating reflectance data, based on detecting the light by the detector structure, by way of a processor contained within the oximeter probe housing and coupled to and powered by the battery;

using the processor, determining an oxygen saturation value for the tissue based on the reflectance data;

using the processor, determining a range of oxygen saturation values from a plurality of ranges of oxygen saturation values which the oxygen saturation value is in, wherein the plurality of ranges of oxygen saturation values are previously stored in a memory coupled to the processor, coupled to and powered by the battery, and housed within the housing; and marking the tissue with ink, from a dispenser that is located on the line that the first and second source structures are positioned on, based on the range in which the oxygen saturation value is in using ink stored in a reservoir contained within the oximeter probe housing and an inking tip positioned on the probe face.

20. The device of claim 19 wherein a ninth distance is from the first source structure to the second source structure, and the ninth distance is greater than the first, second, fifth, sixth, seventh, and eighth distances.

* * * * *